US007776537B2

(12) United States Patent
Joo

(10) Patent No.: US 7,776,537 B2
(45) Date of Patent: Aug. 17, 2010

(54) METHOD OF PREPARING A PRRS VIRUS VACCINE

(75) Inventor: Han-Soo Joo, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 11/751,560

(22) Filed: May 21, 2007

(65) Prior Publication Data
US 2007/0212684 A1 Sep. 13, 2007

Related U.S. Application Data

(62) Division of application No. 11/175,605, filed on Jul. 5, 2005, now Pat. No. 7,241,582.

(51) Int. Cl.
C12Q 1/68 (2006.01)
(52) U.S. Cl. ......................................................... 435/6
(58) Field of Classification Search ........................ None
See application file for complete search history.

(56) References Cited

U.S. PATENT DOCUMENTS 4,562,147 A 12/1985 Joo
5,690,940 A 11/1997 Joo
5,888,513 A * 3/1999 Duran et al. ............. 424/186.1

FOREIGN PATENT DOCUMENTS

WO WO99/39582 A1 8/1999

OTHER PUBLICATIONS

Gilbert et al. Typing of Porcine Reproductive and Respiratory Syndrome Viruses by a Multiplex PCR Assay. Journal of Clinical Microbiology, Jan. 1997, vol. 35, No. 1, pp. 264-267.*
Schommer et al. Comparison of porcine reproductive and respiratory syndrome virus growth in media supplemented with fetal bovine serum or a serum replacement. Journal of Veterinary Diagnostic Investigation, 2001, vol. 13, pp. 276-279.*
Wootton et al. Journal of Virology, Oct. 2002, vol. 76, No. 20, pp. 10569-10576, especially p. 10572.*
Dea S., et al. "Current knowledge on the structural proteins of PRRS virus: comparison of the N. American and European isolates", *Arch Virol* (2000) 145:659-688.
Yoon, I.J., et al. "Isolation of a cytopathic virus from weak-born pigs with a herd history of swine infertility and respiratory syndrome", *J. Vet Diag Invest* (1992) 4:139-143.
Park, B.K., et al. "Pathogenesis of plaque variants of PRRS virus in pregnant sows", *Am J Vet Res* (1996)57:320-323.
Kim, H.S., et al. "Enhanced replication of porcine reproductive and respiratory syndrome virus in a homogeneous subpopulation of MA-104 cell line", *Arch Virol* (1993) 133:477-483.
Choi, K. Yeon, et al. "Relative sensitivity and specificity of agar gel immunodiffusion, enzyme immunosorbent assay, and immunoblotting for detection of anti-bovine leukemia virus antibodies in cattle", *Journal of Virological Methods* (2002) 104:33-39.

Plagemann, Peter, G.W. "Epitope specificity of monoclonal antibodies to the N-protein of porcine reproductive and respiratory syndrome virus determined by ELISA with synthetic peptides", *Veterinary Immunology and Immunopathology* (2005) 104:59-68.
Guiseppe, Antonio De, et al. "Expression of the Bovine Leukemia Virus Envelope Glycoprotein (gp51) by Recombinant Baculovirus and Its Use in an Enzyme-Linked Immunosorbent Assay", *Clinical and Diagnostic Laboratory Immunology* (2004) 11(1):147-151.
Cho, H. J., et al. "An ELISA for Porcine Reproductive and Respiratory Syndrome: Production of Antigen of High Quality", *Can. J. Vet. Res.* (1996) 60:89-93.
Cho, H. J., et al. "Performance of ELISA Antigens Prepared from 8 Isolates of Porcine Reproductive and Respiratory Syndrome Virus with Homologous and Heterologous Antisera", *Can. J. Vet. Res.* (1997) 61:299-304.
IDEXX: "Trousse de Détection de Anticorps dirigés contre le Virus du Syndrome Dysgénésique et Respiratoire Porcine (SDRP/PRRS)", IDEXX, XP002412193 (Dec. 14, 2001) pp. 5-9.
Albina, E. "Le syndrome dysgénésique et respiratoire porcin: dix ans d'expérience (1986-1996) sur une infection virale insolite", *Vet Res.* (1997) 28(4):305-352.
Denac, Helena, et al. "An indirect ELISA for the detection of antibodies against porcine reproductive and respiratory syndrome virus using recombinant nucleocapsid protein as antigen", *Journal of Virological Methods* (1997) 65(2):169-181.
Barfoed, et al., "DNA vaccination of pigs with open reading frame 1-7 of PRRS virus," Vaccine (2004), vol. 22 , pp. 3628-3641, www.elsevier.com/locate/vaccine, Denmark.
Charerntantanakul, et al., "Immune responses and protection by vaccine and various vaccine adjuvant candidates to virulent porcine reproductive and respiratory syndrome virus," Veterinary Immunology and Immunopathology (2006), vol. 109, pp. 99-115, www.elsevier.com/locate/vetimm, USA.
Dewey, et al., "Effects of porcine reproductive respiratory syndrome vaccination in breeding-age animals," Prev Vet Med. (2004), vol. 62(4), pp. 299-307 (Abstract only), Canada.
Fernandez, et al., "Porcine reproductive and respiratory syndrome virus (PRRSV) envelope GP5 protein fails to protect pigs against PRRSV," 4th International Symposium On Emerging and Re-Emerging Pig Diseases (2003), Rome, Italy.
Lopez, et al., "Role of neutralizing antibodies in PRRSV protective immunity," Vet Immunopathol (2004), vol. 102(3), pp. 155-163 (Abstract only), USA.
Nielsen, et al., "Reversion of a live porcine reproductive and respiratory syndrome virus vaccine investigated by parallel mutations," Journal of General Virology (2001), vol. 82, pp. 1263-1272, Great Britain.

(Continued)

Primary Examiner—Ali R. Salimi
(74) Attorney, Agent, or Firm—Patentique PLLC

(57) ABSTRACT

This invention provides kits, devices, and methods for the detection of antibodies that recognize one or more proteins and/or antigens from porcine reproductive and respiratory syndrome virus (PRRSV). The antibodies may be in a biological fluid of a PRRSV infected or at risk subject. The invention may be advantageously applied to both the diagnosis and prevention of PRRSV infection.

12 Claims, 1 Drawing Sheet

OTHER PUBLICATIONS

Nilubol, et al., "The effect of a killed porcine reproductive and respiratory syndrome virus (PRRSV) vaccine treatment on virus shedding in previously PRRSV infected pigs," Vet Microbiol (2004), vol. 102(1-2), pp. 11-18 (Abstract only), USA.

Nodelijk, et al., "A quantitative assessment of the effectiveness of PRRSV vaccination in pigs under experimental conditions," Vaccine (2001) vol. 19(27), pp. 3636-3644 (Abstract only), The Netherlands.

Qiu, et al., "Protective immunity induced by a recombinant pseudorabies virus expressing the GP5 of porcine reproductive and respiratory syndrome virus in piglets," Vet Immunol Immunopathol (2005), vol. 106(3-4), pp. 309-319 (Abstract only), China.

Plana-Duran, et al., "New strategies on vaccinology: Use of the transmissible gastroenteritis virus as a vector for swine diseases," 4th International Symposium On Emerging and Re-Emerging Pig Diseases (2003), Rome, Italy.

Rogan, et al., "Novel vaccines from biotechnology," Rev. Sci. Tech. Off. Int. Epiz. (2005), vol. 24(1), pp. 159-174, Canada.

Scortti, et al., "Effects of two commercial European modified-live vaccines against porcine reproductive and respiratory syndrome viruses in pregnant gilts," Vet J. (2006) vol. 172(3), pp. 506-514 (Abstract only), Spain.

Wagner, et al., "Protection against heterologous PRRSV challenge in pregnant sows immunized with multivalent PRRS vaccine," International PRRS Symposium, St. Louis, MO (Dec. 2-3, 2005), USA.

Zhang, et al., "Monoclonal antibodies against conformationally dependent epitopes on porcine reproductive and respiratory syndrome virus," Veterinary Microbiology (1998), vol. 63, pp. 125-136, USA.

* cited by examiner

Immunodiffusion enzyme assay (IDEA)

- Vertical IDEA
- Horizontal IDEA

Samples 1, 2 and 3 show positive, negative, and positive results, respectively.

METHOD OF PREPARING A PRRS VIRUS VACCINE

CROSS-REFERENCES TO RELATED APPLICATIONS

This application is a divisional of U.S. patent application Ser. No. 11/175,605, filed Jul. 5, 2005. This application is hereby incorporated by reference in its entirety as if fully set forth.

FIELD OF THE INVENTION

This invention relates to kits, devices, and methods for the detection of antibodies that recognize one or more proteins and/or antigens from porcine reproductive and respiratory syndrome virus (PRRSV). The antibodies may be in a biological fluid of a PRRSV infected or at risk subject. The invention may be advantageously applied to both the diagnosis and prevention of PRRSV infection.

BACKGROUND OF THE INVENTION

A major cause of economic losses in the U.S. swine industry is porcine reproductive and respiratory syndrome (PRRS) virus, or PRRSV. PRRSV is the causative agent of reproductive failure and respiratory disorders in pigs. The economic losses associated with PRRS are mainly due to its involvement in abortion in pregnant females and respiratory disease complex (PRDC) in growing pigs. Different control measures including the use of vaccine and management change have been practiced. See U.S. Pat. No. 5,690,940, for example. Despite routine vaccination, however, it is not uncommon for outbreaks of PRRSV to occur on swine farms.

The outbreaks are most commonly due to the failure of bio-security measures. Poor detection of PRRSV infected replacement gilts into herds has been a common source of bio-security failure. These problems may be prevented if a simple and inexpensive method to test for PRRSV infection was available on farms. Such a method may also be applied to testing whether sows are producing negative weaned pigs and during acclimatization procedures.

In order to test PRRSV antibody, veterinarians should collect blood samples and send them to a veterinary diagnostic laboratory. At present, ELISA, indirect fluorescent antibody test and immunoperoxidase monolayer assay are common laboratory methods to detect anti-PRRSV antibody. However, these methods require expensive equipment and trained laboratory techniques. Using these techniques, at least 3 days including mailing time are required to obtain a result. In addition, swine farmers have to incur costs for collecting samples and shipping them to a diagnostic laboratory. A field-based, simple and rapid test for the detection of PRRSV antibodies would be very useful in laboratories of veterinary clinics or corporate swine farms. Eradication of the disease using PRRSV vaccine has not been routinely successful at the farm level. Methods such as total depopulation and repopulation have shown to be effective for on-farm eradication. However, such methods cannot be used in every farm and is relatively expensive to perform.

Moreover, such methods are dependent upon detection of PRRSV. The nucleic acid sequences and encoded proteins of some PRRSV strains have been described. The detection of PRRSV via tissue samples, including lung tissue, has also been discussed (see WO 96/06619), which is consistent with the observation that PRRSV preferentially replicates in alveolar lung macrophages. After infection by the oronasal route, PRRSV replicated in lung macrophages proceed to the lung lymph nodes and then to different organs via blood stream.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

The present invention relates to kits, devices, and methods for the detection of infection of a subject by porcine reproductive and respiratory syndrome (PRRS) virus, or PRRSV. The detection is mediated by the use of compositions containing one or more PRRSV encoded proteins and/or antigens which binds antibodies against said proteins. Thus the invention may be viewed as based upon the principle of "antibody capture" followed by detection of the antibodies. The antibodies are those which are present in a subject infected with PRRSV but absent in uninfected individuals.

The one or more PRRSV encoded proteins may include the nucleocapsid (N) protein and/or one or more viral envelope ("E") proteins. The proteins may also be glycoproteins found on the surface of PRRSV infected cells. The proteins may also be considered PRRSV antigens used to detected antibodies in a subject, where the antibodies recognize the PRRSV proteins and thus PRRSV.

The PRRSV protein(s) and/or antigens may be used advantageously in kits, devices, and methods of the invention to detect PRRSV infection at early time points, based upon the detection of anti-PRRSV antibodies. Such detection methods rely upon the presence of antibodies, in an infected subject at an early time post infection, against at least one PRRSV protein and/or antigens as described herein.

In a first aspect, the invention provides a method of using the compositions containing one or more PRRSV expressed proteins and/or antigens in the preparation or use of a kit or device as described herein. In some embodiments, the device is a dish that is coated with a composition of the invention. Non-limiting examples of such dishes include Petri dishes of various sizes as well as the wells of a microtiter plate. The dish may be for use in a diagnostic test for antibodies against one or more PRRSV proteins and/or antigens contained in the composition. Thus, such devices may be used to detect the presence of antibodies against one or more PRRSV proteins and/or antigens in the composition. The antibodies to be detected may be in a sample of a biological fluid, and if the antibodies are present, it serves as an indicator of PRRSV infection in the subject from which the sample was taken. Thus the devices may be used as a rapid means of diagnosing the presence of PRRSV infection.

At the heart of such a device of the invention is the presence of an immobilized form of one or more PRRSV proteins and/or antigens present in the composition. A PRRSV protein and/or antigen may be immobilized directly, such as by adsorption (e.g. coating) or by conjugation to a surface of a device as non-limiting examples. Alternatively, the protein and/or antigen may be indirectly immobilized, such as by use of an agent which binds the protein and/or antigen or by use of a linker that binds both the surface and the protein or antigen. Thus the immobilized PRRSV protein(s) and/or antigen(s) may be viewed as a "capture agent" for binding by an antibody against the protein(s) and/or antigen(s) to form an immobilized complex containing the protein(s) and/or antigen(s). The immobilized "capture agent" may of course be viewed as an agent to "capture" an antibody which binds the agent.

The complex may then be detected by use of a "detector agent", such as a labeled reagent which binds the complex, as described herein. If bound to a complex, the "detector agent" indicates the presence of anti-PRRSV antibody in a sample. In some embodiments, the "detector agent" is a labeled secondary antibody which binds the antibodies, if present in the sample, which have been immobilized as part of the complex. The presence of anti-PRRSV antibody may be used as an indication of PRRSV infection in the subject from which the sample was obtained. The absence of anti-PRRSV antibody would indicate the absence of infection. The sample is preferably from a porcine subject, or other subject suspected of being infected with PRRSV, but any subject which may be infected by PRRSV or a PRRSV carrier may be used in the devices of the invention.

The "detector agent" may be labeled to permit direct detection, such as by conjugation to a particulate label which is visible to the eye upon sufficient aggregation. Alternatively, the agent may be labeled for indirect detection, such as by conjugation to an enzyme which is detected based upon its activity on a detectable substrate or to produce a detectable product. Of course the "detector agent" may be a "secondary agent" which binds a labeled or unlabeled "primary" binding agent which binds the complex of the invention.

A device of the invention may also contain a control site or control region within the device of the invention which confirms the proper functioning of the device regardless of whether PRRSV antibodies were present in a sample applied to the device. Such a control may be based upon the detection of another molecular or macromolecular entity present in the sample.

Without being bound by the format of the device used, the PRRSV protein(s) and/or antigen(s), and compositions comprising it/them, of the invention may also be used in a method of detecting antibodies against the PRRSV protein(s) and/or antigen(s). Such methods may be designed to detect such antibodies in a biological fluid from a subject, such as an individual suspected of being infected with PRRSV. The method comprises contacting the sample, or a diluted form thereof, with the PRRSV encoded protein(s) and/or antigen(s) and determining whether there are any antibodies in the sample which bind the protein(s) and/or antigen(s). The binding of an antibody to a PRRSV protein and/or antigen forms a complex, which may be detected to indicate the presence of the antibody, and thus indicated the presence of a PRRSV infection in the subject from which the sample was obtained. The sample is preferably from a porcine subject, but any subject which may be infected by PRRSV or a PRRSV carrier may be used in relation to the present invention.

The range of biological fluids which may be used in the practice of the invention includes any fluid in which antibodies against a PRRSV protein and/or antigen may be detectably present. Non-limiting examples include the bodily secretions of a subject, such as blood, serum, plasma, saliva, tears, mucous, nasal discharge, and vaginal secretions. Dilutions of such fluids may of course also be used as the sample in the practice of the invention. In some embodiments, a diluent containing EDTA or other divalent cation chelator used in a 1:1 ratio with a sample of biological fluid from a subject. In embodiments with serum or plasma samples, dilution may be omitted.

The sample is preferably from an individual suspected of being infected with PRRSV due to the presence of symptoms indicative of an infection. Alternatively, the methods of the invention may be used as part of routine screening of animals, such as those of a farm to permit rapid identification and isolation of infected individuals. The methods may also be used in specific instances, such as prior to transport or transfer of an animal from one location to another to permit identification of infection and prevent spread of infection. In many embodiments of the invention, the subject is a pig, and thus the sample may be of a bodily fluid or secretion from a pig. Non-limiting examples of pigs that from which samples may be obtained for use with the present invention include boar, gilt, sow, fattener, nursery and suckling pigs. The pigs may range in any age from birth to death. Non-limiting examples include pigs of about 30 to about 40, 41 to about 50, or 51 to about 60 days or older may be used in the practice of the invention.

In some embodiments, the method is a vertical immunodiffusion enzyme assay (VIDEA) based format. The format utilizes immobilized PRRSV protein and/or antigen which is separated by a permeable barrier from a sample containing, or suspected of containing, anti-PRRSV antibodies. The sample is presented to the barrier via a porous material, and anti-PRRSV antibodies in the sample diffuse through the permeable barrier to come into contact with the PRRSV protein and/or antigen. Contact between the antibodies and the protein/antigen results in the formation of a complex, which is subsequently detected to indicate the presence of the antibodies in the sample. The detection may be in the form of an area wherein the complexes are present. In some embodiments, the permeable barrier is agar or agarose.

In other embodiments, the method is a horizontal immunodiffusion enzyme assay (HIDEA) based format. The format is similar to that of VIDEA described above in that both utilize immobilized PRRSV protein and/or antigen. The HIDEA format includes the separation, by a permeable barrier, of the immobilized protein/antigen from a sample containing, or suspected of containing, anti-PRRSV antibodies. The sample is presented to the barrier directly, such that the anti-PRRSV antibodies diffuse through the permeable barrier to come into contact with the PRRSV protein and/or antigen. The diffusion may also radiate outward from the point of sample contact to the barrier. Contact between the antibodies and the protein/antigen results in the formation of a complex, which may be detected to indicate the presence of the antibodies in the sample. The detection may be in the form of a circle or ring in which the complexes are present. In some embodiments, the permeable barrier is agar or agarose.

The various aspects of the invention are contemplated for use in relation to all PRRSV strains that are antigenically related to the North American strains. Therefore, the invention may be more generally viewed as based on the protein(s) of any PRRSV virus.

Additionally, methods relating to the production of such devices are provided. Thus additional aspects of the invention related to methods of preparing components of the kits, devices and methods described herein. The invention includes a method of preparing PRRSV proteins from cells infected therewith. In some embodiments, the proteins are harvested at an early time point after infection when the majority, or entirety, of the proteins remain associated with the infected cells. Stated differently, the majority or entirety of PRRSV encoded proteins are either within the infected cells or associated with the cell membrane of the infected cells. Under such conditions, relatively few, if any, PRRSV particles are present in the extracellular environment outside the cells.

Another aspect provides methods for the immobilization of a first binding agent, such as, but not limited to, the N protein and/or one or more envelope proteins of PRRSV, on at least one surface of a device as described herein.

In other aspects of the invention, kits comprising the devices of the invention or for the practice of the methods described herein are provided. Additional aspects include compositions and articles of manufacture for use in the practice of one or more methods provided by the invention. Non-limiting examples of such compositions include those for use in the preparation of a kit or device of the invention. Non-limiting examples of kits include those comprising one or more compositions or agents of the invention, or one or more devices of the invention, for use in the methods disclosed herein.

The details of one or more embodiments of the invention are set forth in the accompanying drawings and the description below. Other features, objects, and advantages of the invention will be apparent from the drawings and detailed description, and from the claims.

DEFINITIONS

Figure 1:
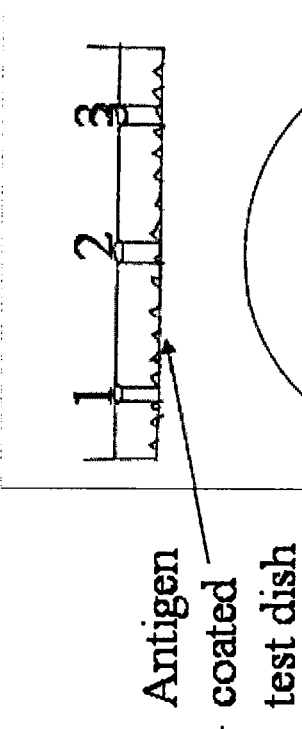
FIG. 1 is a schematic representation of two immunodiffusion enzyme assays (IDEAs). The vertical (VIDEA) and horizontal (HIDEA) embodiments are shown, along with a representation of how positions 1, 2, and 3 show positive, negative, and positive results, respectively.
Figure 1:
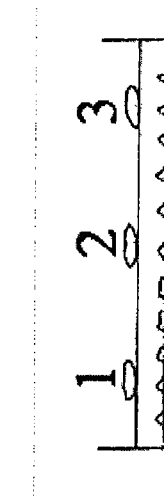
Figure 1:
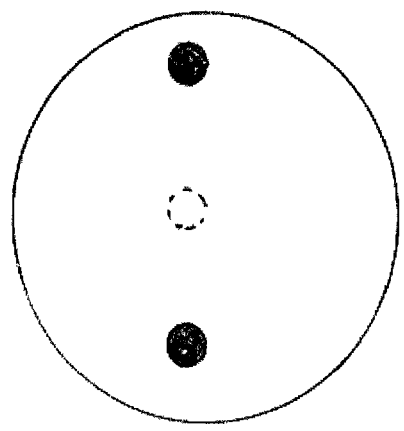

As used herein, the terms porcine reproductive and respiratory syndrome (PRRS) virus, or PRRSV, refer to a virus which causes PRRS, Mystery Swine Disease (MSD), Swine Infertility and Respiratory Syndrome (SIRS) which was previously known as "blue-eared syndrome", porcine epidemic abortion and respiratory syndrome (PEARS), Wabash syndrome, mystery pig disease (MPD), swine plague, blue abortion disease or blue ear disease in the United Kingdom, abortus blau in the Netherlands, seuchenhafter spatabort der schweine in Germany, and Heko-Heko disease.

PRRSV protein refers to any polypeptide product encoded by the PRRSV genome and/or produced as only as a result of PRRSV infection or the PRRSV lifecycle. Thus PRRSV specific, and thus not encoded by or expressed by a PRRSV infected cell, polypeptides are within the scope of the term. Endogenous polypeptides encoded by a PRRSV infected cell, but not expressed in the absence of PRRSV infection and/or lifecycle, are not intended. However, endogenous polypeptides expressed only as a consequence of PRRSV infection and/or lifecycle are within the scope of the term. The term also includes alternative forms of the polypeptides due to changes in secondary and/or tertiary structure, such as those resulting from partial or substantial protein denaturation as a non-limiting example. Thus denatured forms of the polypeptides are within the scope of the term.

PRRSV antigen refers to any portion or fragment of a PRRSV polypeptide that is recognized by an anti-PRRSV antibody. In some cases, the portion or fragment may be a peptide with an attached moiety, such as, but not limited to, a sugar moiety, a phosphate moiety, or a lipid moiety. Alternatively, the portion or fragment may be a peptide without any attached non-peptide moieties.

DETAILED DESCRIPTION OF MODES OF PRACTICING THE INVENTION

The invention relates to kits, devices, and methods directed to the detection anti-PRRSV antibodies. The detection is based upon the use of one or more PRRSV encoded proteins and/or antigens which binds antibodies against said proteins. The antibodies are those present in a PRRSV infected subject but absent in uninfected individuals. The invention may be viewed as an "antibody capture" assay wherein the captured antibody is detected. The invention also may be considered as providing immunodiffusion based methods for the detection of anti-PRRSV antibodies.

The invention is based in part upon the recognition that the structural proteins of PRRSV, including the nucleocapsid (N), membrane (M) associated and at least 4 envelope (E) proteins may be used to detect antibodies in a PRRSV infected subject. Stated differently, the invention is based in part on the discovery that antibodies against these proteins, and/or antigenic portions thereof, are present in PRRSV infected subjects such that detection of the antibodies provides an advantageous means to indicate that a subject is infected with PRRSV.

The invention is also based in part on the discovery that certain conditions and protocols may be used to obtain a composition of PRRSV proteins and/or antigens that contains a high concentration of E proteins relative to other PRRSV proteins and/or antigens. Thus the invention includes a method of preparing PRRSV proteins and/or antigens from cells infected therewith. The proteins and/or antigens are harvested at an early time point after infection when the majority, or entirety, of the proteins remain associated with the infected cells or are otherwise part of a cell associated viral component (CAVC) of the invention. Stated differently, the majority or entirety of PRRSV proteins and/or antigens are either within the infected cells or associated with the cell membrane of the infected cells. Under such conditions, relatively few, if any, PRRSV particles are present in the extracellular environment outside the cells. The invention is based in part on the unexpected discovery that cells infected for a relatively short period of time can produce sufficient amounts of PRRSV encoded proteins that are suitable for use in the detection methods of the invention. The preparation of CAVC from an early time point, before the production of PRRSV particles and/or the release thereof into the extracellular environment also has the benefit of increased safety in that no infectious viral particles are present as a contaminant.

The infected cell may be any that is capable of being productively infected by PRRSV. Non-limiting examples include porcine cells, either in vitro or in vivo. One non-limiting example of cells in vitro is primary cells from a porcine subject that are infected with PRRSV. A non-limiting example of cells in vivo are porcine alveolar macrophages (PAMs) which are infected with PRRSV via an oronasal route and then subsequently harvested for preparation of PRRSV proteins and/or antigens. Another non-limiting example is with the use of the simian cell line MARC-145. The PRRSV proteins and/or antigens produced by the method include at least one of the PRRSV N, M, and E proteins. Combinations of these proteins may also be prepared from cells of the invention. In some embodiments, the prepared proteins/antigens have a high ratio of E proteins relative to N and M proteins.

Thus the invention provides a method of preparing PRRS virus proteins and antigens from PRRS virus infected cells, where the method comprises a) providing a population of cells infected with PRRS virus; b) isolating the infected cells away from cell-free PRRS virus to form cells containing cell associated PRRS virus proteins and antigens; and c) extracting or eluting PRRS virus proteins and antigens from the cells isolated in part b). In cases wherein there is no cell-free virus present, then part b) may be modified to simply be an act of isolating the cells from other materials which may interfere with the method, such as the culture medium used with the cells. Part b) may be performed by any means known in the art, such as by use of centrifugation to generate a cell pellet and supernatant that is removed or discarded or by use of a membrane filtration to remove the supernatant and retain the cells. Part c) is optionally performed by resuspension of cells in a buffer. In some embodiments, the extraction or elution is with a detergent containing solution, thus the buffer used to resuspend cells may contain detergent.

In other embodiments, the method comprises use of a population of cells that has been infected with PRRS virus for a sufficient time to produce little to undetectable amounts of infectious units per ml of supernatant, such as the culture media used with the cells. Non-limiting examples include less than $10^{1.5}$ tissue culture infective dose $(TCID)_{50}$/ml). The population of cells used in the method may optionally have been infected with PRRS virus for a sufficient time to observe CPE. Of course cells that have not been infected long enough for CPE, or early stages of CPE, to be observed may also be used in the practice of the invention.

In a further embodiment, the invention provides a method of preparing PRRS virus proteins and antigens from PRRS virus infected pig alveolar macrophage (PAM) cells. The method may comprise preparing said proteins and antigens from a population of PAM cells obtained by lung lavage of a pig oronasally inoculated with PRRS virus. The PRRS virus proteins and antigens may be extracted or eluted from the cells as described above. Thus the cells may be resuspended in an extraction buffer. In some embodiments, the extraction or elution is with a detergent containing solution, thus the buffer used to resuspend cells may contain detergent.

The detergent containing solution may be any that is suitable for extracting or eluting PRRSV proteins and/or antigens. One non-limiting example is the use of a non-ionic detergent, like poly(ethylene glycol) p-isooctyl-phenyl ether, octylphenoxypolyethoxyethanol (Nonidet P-40), or Triton X-100. In some embodiments of the invention, the detergent is at a concentration of about 0.5% in solution, such as a solution of about 0.5% Triton X-100.

The invention also provides a method of preparing PRRS virus proteins and antigens from PRRS virus infected cells. Such a method comprises preparing said proteins and antigens from a population of the cells prepared by in vitro and in vivo methods. For the in vitro method, pig alveolar macrophage (PAM) cells or MARC-145 line cells are cultured, and the cells are harvested following an infection of PRRSV. For the in vivo method without using a cell culture system, PAM cells obtained by lung lavage of a pig following inoculation of PRRS virus oronasally. The antigen yields were compared using different PRRSV isolates and different days after virus inoculation, and optimal conditions for the highest antigenic yields were predetermined by comparative testings.

The invention of course includes compositions containing the isolated PRRSV proteins and/or antigens prepared by any of the methods disclosed herein. The compositions may be used for any purpose for which PRRSV proteins and/or antigens are used. Non-limiting examples include use to prepare antibodies against the proteins/antigens; use as reference markers for PRRSV proteins; and use as an immunogenic compositions, such as in the case of a vaccine formulation, optionally with a suitable adjuvant, that is administered to an animal to generate an immune response. Additional non-limiting examples of the compositions include those where the protein(s)/antigen(s) is/are in soluble or lyophilized (freeze dried) form.

In some embodiments, the composition is in a solution suitable for coating a surface, such as a surface of a device of the invention. Such solutions allow the proteins to be coated on the bottom of Petri dishes. Non-limiting examples include solutions of dilute PRRSV proteins/antigens in 0.06M carbonate buffer solution at pH 9.6. The solutions may be used to coat the surface of a dish or well, such as those of polystyrene or glass Petri dishes or multi-well plates, respectively. Non-adsorbed material may be poured off, optionally followed by one or more washes in buffered solution without the proteins/antigens. The coating may be conducted at various temperatures, including those below 25° C., for various time periods. In some embodiments, coating may be at or about 4° C. for about 72 hours.

Thus the invention also provides a method of coating a surface with virus protein(s) and/or antigen(s), said method comprising a) providing a solution containing one or more PRRS virus proteins and antigens prepared as described herein; and b) contacting said solution with a surface for a period of time to allow said proteins and antigens to adsorb to the surface of said dish. In some embodiments, the protein(s) and/or antigen(s) were extracted or eluted from PRRSV infected cells by use of a detergent containing solution as described herein. In further embodiments, the surface to be coated is made of polystyrene or glass or similar material. The surface is preferably washed with ethanol which is then dried off.

A solution of PRRSV proteins/antigens is applied to the clean surface and allowed to adsorb for from about 2 to about 4 hours to overnight. The proteins/antigens may be diluted to an optimum concentration between about 0.01 to 0.001%, preferably in a sodium bicarbonate-sodium carbonate coating buffer to promote adherence of the proteins/antigens to the surface. The coating buffer should preferably be between about 0.01M to 0.1M (pH 9 to 10) containing from about 0.84 to 8.4 grams per liter of $NaHCO_3$ and 0.11 to 10.6 grams per liter of $Na_2CO_3$. After the coating period, the excess solution is poured off or otherwise removed. The coated surface may be washed with distilled water or buffer without the proteins/antigens. The coating with PRRSV protein(s) and/or antigen(s) may be optionally followed by coating with a blocking agent, such as, but not limited to, 1% bovine serum albumin (BSA) in phosphate-buffered saline (PBS), pH 7.2. The coating may be conducted at various temperatures, including those of about 37° C., for various time periods. In some embodiments, coating may be at or about 37° C. for about 1 hour. After the application of blocking agent, the solution is removed and optionally followed by one or more water washed or washes comprising buffer solution without the agent.

After coating, a permeable barrier layer is applied to the coated surface. The barrier may be applied as a solution which later forms a permeable barrier after drying. Non-limiting examples include solutions of agar and/or agarose which when dried form a permeable barrier composed of a gel like material. Thus a melted agar or agarose layer may be applied and permitted to solidify. The depth of the agar layer is not critical and may vary from at least about 1.5 mm and preferably about 2 mm up to about 10 mm. The layer is applied from solution between about 0.75 to 1.5% and preferably about 1%.

As a non-limiting example with polystyrene petri-dishes that are 60 mm in diameter, 4 ml of 0.6% agarose in PBS is used for VIDEA based methods as described herein. Six (6) ml of the same solution is used for HIDEA based methods. The solution is allowed to solidify, such as at 4° C., overnight.

Devices that are so coated may be stored, such as at 4° C. in a moisture chamber, for up to 4 months.

A device with a coated surface as described herein may be used as all or part of a diagnostic kit for the detection of anti-PRRSV antibodies. The invention thus also provides a method of detecting antibodies to PRRS virus which method comprises a) collecting a blood or blood serum sample from a subject; b) contacting said sample with a permeable barrier of a coated device as described herein; c) incubating said sample to allow diffusion of molecules such as antibodies through the permeable barrier and bind the protein(s)/antigen(s) used to coat the device; d) removing the permeable barrier and optionally washing the device to remove unbound antibodies; e) detecting complexes formed by the binding of antibodies to the protein(s)/antigen(s). With respect to the device in part b), one non-limiting example is where the device is a dish test plate comprising (1) a dish having a flat supporting surface; (2) a coating adsorbed on said surface of PRRSV protein(s)/antigen(s); and (3) a layer of agar overlaying said coating.

Regarding part e), the method may be practiced with application of a detector agent that binds the formed complexes. One non-limiting example is with the use of a secondary antibody that binds antibodies that may be present in the sample. Non-limiting examples of such secondary antibodies include those from specific animals, e.g., mouse, rat, goat, rabbit, etc., which recognize the Fc portions of the antibodies in the sample tested.

The secondary antibody may be conjugated to a label to facilitate its detection. The conjugation modifies the antibody by attachment of another moiety thereto. The moiety is preferably a detectable label, including a directly detectable label such as a radioactive isotope, a fluorescent label (Cy3 and Cy5 as non-limiting examples) or a particulate label. Non-limiting examples of particulate labels include latex particles, metal sols, and colloidal gold particles. Alternatively, the label may be for indirect detection. Non-limiting examples include an enzyme, such as, but not limited to, peroxidase, luciferase, alkaline phosphatase, and horse radish peroxidase. Other non-limiting examples include a molecule bound by another molecule, such as, but not limited to, biotin, an affinity peptide, or a purification tag. Preferably, the label is covalently attached.

In some embodiments, the secondary antibody is an enzyme conjugated anti-swine immunoglobulin which is allowed to bind the antibodies in the complexes for about 30 to about 60 minutes. After binding, unbound secondary antibody may be removed by one or more optional washes. The enzyme may be any suitable enzyme, such as the enzymes used in enzyme linked immunosorbent assays (ELISAs), including a peroxidase. Peroxidase produces a purple color when reacted with aminosalicylic acid and hydrogen peroxide, or p-phenylene diamine and hydrogen peroxide. Alkaline phosphatase produces a yellow color when reacted with dinitrophenylphosphate. Beta-galactosidase reacts with O-nitrophenyl-.beta.-D-galactopyranoside to give a purple color.

Continuing with the non-limiting example of an enzyme linked secondary antibody, detection of a complex by detection of the bound secondary antibody may be mediated by overlaying an agar solution containing a substrate which is reacted upon by the enzyme to produce a detectable signal, such as color production as a non-limiting example. In some embodiments, the detectable signal is visually observable, such as by the unaided eye. The signal may be compared to the color reaction observed with the use of positive controls (containing known anti-PRRSV antibodies which bind the coated surface) and/or negative controls containing no such anti-PRRSV antibodies.

In some embodiments of the invention, particularly the VIDEA as described herein, the sample is collected and applied to (or is collected by) a porous material such as, but not limited to, filter paper or a filter paper disc. With the use of paper discs as a non-limiting example, the disc is placed flat on the permeable barrier to allow molecules to diffuse from the disc, through the barrier, and to the coated surface. At the surface, molecules (like antibodies) from the sample which bind to PRRSV proteins/antigens of the invention form complexes with the proteins/antigens. Thus the molecules from the sample become immobilized to the coated surface. In some embodiments, the period of time for diffusion and complex formation is about 2 to about 3 hours at either about room temperature (25° C.) or about 37° C.

After complex formation, the permeable barrier is removed. In some embodiments comprising an agar or agarose barrier, the layer of agar or agarose may be peeled off followed by the optional washes.

The methods of the invention are based upon the formation of a complex comprising the PRRSV proteins/antigens bound to anti-PRRSV antibodies of a sample as described herein. The anti-PRRSV antibodies may be detected to improve the ease of detecting the complex. Detection of a complex of PRRSV proteins/antigens and anti-PRRSV antibodies from a sample indicates the presence of PRRSV infection in the subject from which the sample was obtained.

The invention further provides a vertical immunodiffusion enzyme assay (VIDEA) method, said method comprising a) providing a diagnostic device comprising at least one surface coated with one or more PRRSV proteins and antigens as described herein, said surface having been overlaid with a permeable barrier as described herein; b) contacting the surface of the barrier with a porous material comprising an antibody containing sample derived from a subject; c) incubating said device for a period sufficient to allow diffusion of material from said sample to said one or more surface, said period optionally occurring after removal of the porous material; and d) detecting the presence of antibodies at the surface of the dish after removal of the permeable barrier. In some embodiments, the porous material is a paper disk.

The invention further provides a horizontal immunodiffusion enzyme assay (HIDEA) method, said method comprising a) providing a diagnostic device comprising at least one surface coated with one or more PRRSV proteins and antigens as described herein, said surface having been overlaid with a permeable barrier as described herein but comprising one or more indentations, for receiving a sample, on said surface; b) contacting the one or more indentations with an antibody containing sample derived from a subject; c) incubating said device for a period sufficient to allow diffusion of material from said sample to said one or more surface; and d) detecting the presence of antibodies at the surface of the dish after removal of the permeable barrier. In some embodiments, from one to a plurality of small diameter holes are punched out of the permeable barrier to form indentations that function as test sample wells. The wells may be about 1 to 4 mm in diameter, for example, and penetrate through the agar coating. The use of a template with seven 3-mm circular wells to punched holes onto the agar of each testing dish for HIDEA is one non-limiting example.

In both VIDEA and HIDEA embodiments, the sample is a serum sample or a whole blood sample. The methods may be applied to samples from a variety of animals and/or subjects that may have been infected with PRRSV or that are suspected of being infected with PRRS virus. The diagnostic device may be a dish, plate, or well of a plate. Both positive and negative controls may be run with each set of test samples. The same amount of control serum is placed in other wells on the test device.

After incubation of the plates, the agar gel layer is peeled off and the plates are washed, such as with a washing buffer such as Tween 20 in phosphate buffered saline as a non-limiting example. Plates may be washed with distilled or tap water rather than washing buffer. Washing removes unbound (non-specific) antibodies as well as other contaminants.

Both the VIDEA and HIDEA formats include the use of an antigen-antibody reaction to form a complex, which may be detected by use of a detecting agent, such as a secondary antibody, to bind the complex, such as by binding the antibody portion of the complex. The detector agent may be kept in contact with complexes for about 30 minutes to about 2 hours at room temperature. The plates are then washed, such as with buffered washing solution as a non-limiting example to remove unbound conjugate. The washing liquid may be added slowly from the edge of the test plate with a syringe or pipette and poured off. This is optionally repeated up to three times or more.

While the detector agent is incubating, an agar or agarose coating is prepared. As a non-limiting example, a 1% solution of agar, preferably in phosphate buffered saline, is melted and a substrate for the enzyme of the conjugate is incorporated. In some embodiments, a catalyst is incorporated as needed. As a non-limiting example, when the enzyme is a peroxidase, the 1% agar solution may contain between about 0.05 to 0.10% of 5-aminosalicylic acid as the substrate and between about 0.002 and 0.01% hydrogen peroxide as catalyst. The use of about 0.08% substrate and about 0.005% catalyst may also be used. The agar is poured over the washed surface and allowed to solidify.

A color reaction between the enzyme of the secondary antibody occurs within the agar support layer. The reaction aids in the visualization by an enzyme-substrate reaction. The diameters of dark purple circular zones were measured for HIDEA and the presence or absence or color density were recorded for VIDEA to determine antibody quantities.

In the case of HIDEA, the color develops in the form of a circular zone or ring. The rings are dark enough to measure within about 5 to about 30 minutes of the substrate reaction. Upon standing for longer periods, the ring will become darker but will not enlarge. The diameter of the ring produced is related to the amount of specific antibody present in the blood (i.e., virus neutralization titer). The diameter of the dark colored circular zone is measured and used to correlate with a standard virus neutralization test antibody value. The values determined are related to the size of the sample well in the test plate and the size of the sample used. A table of values and/or depictions of representative rings may be included with each device of the invention or with each kit of the invention.

The detecting of the presence of antibodies at the surface in both the VIDEA and HIDEA formats is meant to detect antibodies bound to PRRSV protein(s)/antigen(s) on the surface. The detection may be performed by any means described herein, including the use of a labeled secondary antibody. Other non-limiting means include the visualization of an antigen-antibody reaction via an enzyme-substrate reaction, while the presence of color reaction or density from the reaction is used to indicate the amount (quantitative or semi-quantitative) or presence (qualitative) of anti-PRRSV antibodies.

The PRRSV proteins/antigens as well as compositions, methods, and devices comprising the proteins/antigens are suitable for the preparation of kits produced in accordance with well known procedures. The invention thus provides kits comprising the PRRSV proteins/antigens as described herein, or compositions or devices comprising them, for use in one or more methods as disclosed herein. Such kits optionally further comprise an identifying description or label or instructions relating to their use in the methods of the present invention. Such a kit may comprise containers, each with one or more of the various reagents (typically in concentrated form) or devices utilized in the methods. A set of instructions will also typically be included.

Kits comprising a device of the invention may further comprise one or more additional reagents or pieces of equipment for use with the device in a method of the invention. Non-limiting examples of additional materials for inclusion are sample diluent solution, diluent vial, and a dropper for transfer of sample. Other non-limiting examples include porous materials for use with the VIDEA format and secondary antibodies.

Having now generally described the invention, the same will be more readily understood through reference to the following examples which are provided by way of illustration, and are not intended to be limiting of the present invention, unless specified.

EXAMPLES

Example 1

Preparation of PRRSV Proteins and Dishes

PRRSV proteins may be prepared by use of a PRRSV strain to inoculate susceptible cells in vitro or in vivo and harvesting infected cells at an optimal time to prepare cell associated viral components. For in vitro methods, the antigen may be prepared by a cell culture system or by the use of recombinant technologies. Alternatively, PRRSV infected pig alveolar macrophage (PAM) cells can be obtained from pigs following oronasal inoculation with PRRSV and washing the lung (lung lavage).

The cells were pelleted by centrifugation, and the supernatant removed or discarded. The pellets may be optionally washed. Cell pellets were suspended in a 0.05M tris(hydroxymethyl)aminomethane 0.025M EDTA buffer containing 0.5% Triton X-100 at a volume of 5-10 times that of the packed cells. The mixture was stirred for 2-15 hours at 4° C. and centrifuged at 10,000 g for 1 hour. The supernatant was used as PRRSV antigen. The antigen is non-infectious allowing wide use without a risk of viral spreading.

A dilution of PRRSV protein/antigen in 0.06M carbonate buffer solution at about pH 9.6 was pre-determined by comparative tests. The antigen was coated on polystyrene petri-dishes (60 mm in diameter) by adsorbing at 4° C. for 72 hours. Unadsorbed antigen was poured off, and the dishes were incubated with a blocking agent (e.g. 1% bovine serum albumin, BSA) in phosphate-buffered saline (PBS, pH 7.2) for 1 hour at 37° C. After removing the BSA, 6 ml for HIDEA and 4 ml for VIDEA of 0.6% agarose in PBS was overlayed in the petri-dishes. The agar was allowed to solidify at 4° C. overnight. Using a template, seven 3-mm circular wells were punched onto the agar of each testing dish for HIDEA. For VIDEA, the dishes without wells were used. All of the test dishes were stored at 4° C. in a moisture chamber for up to 4 months.

Example 2

VIDEA

Test plates were prepared by coating viral antigens on the bottom of Petri dishes followed by an overlaying of agar gel generally as described above. In use, a filter paper disc is soaked with test serum from pigs and placed on the agar of the test plate. The flatness of the disc presents a nearly two dimensional starting area such that the contents of a sample like a test serum would move generally in one direction through the agar and toward the coated surface.

The gel was peeled off after an incubation period and the dishes were washed 3 times with 5 to 8 ml of washing solution (PBS containing 0.05% Tween-20). Then 3 ml of commercially available peroxidase-conjugated rabbit anti-pig IgG (1 to 2 µg/ml) diluted in PBS was applied for 45 minutes at 25° C. After the dishes were washed again 3 times with washing solution, 5 ml of 1% agar in PBS containing substrate (5-aminosalicylic acid) and $H_2O_2$ at concentrations of 0.08% and 0.005%, respectively, was overlaid onto the dishes. The presence or absence or color density were recorded for VIDEA In one experiment, the incubation was at 25 or 37° C. for about 2 to 3 hours after which the agar was peeled off. The peroxidase reaction results were determined after about 5 to 10 minutes based on positive samples showing a color reaction. Various serum samples with known ELISA S/P ratios or history of PRRS virus infection were tested along with samples from naïve animals. The sensitivity and specificity of VIDEA was evaluated with respect to ELISA. Table 1 below summarizes the results of this VIDEA and the corresponding ELISA S/P ratios for various pig sera. The percent agreement between the assay results are shown in parentheses. VIDEA showed 100% specificity for pig sera found to be negative in the ELISA. Incubation at 25° C. for about 3 hours showed 100% agreement for all samples when compared to the ELISA.

TABLE 1

| ELISA OD | No. of sera | VIDEA 37° C., 2 hrs positive | VIDEA 37° C., 2 hrs negative | VIDEA 25° C., 3 hrs positive | VIDEA 25° C., 3 hrs negative |
|---|---|---|---|---|---|
| Naive | 40 | 0 | 40 (100%) | 0 | 40 (100%) |
| <0.4 | 30 | 20 (66.6%) | 10 (33.3%) | 30 (100%) | 0 |
| 0.4-0.9 | 32 | 31 (96.9%) | 1 (3.1%) | 32 (100%) | 0 |
| 1.0-1.9 | 17 | 17 (100%) | 0 | 17 (100%) | 0 |
| >2.0 | 10 | 10 (100%) | 0 | 10 (100%) | 0 |

Antigen-antibody reactions occurred in as little as 2 hours, however, longer times appear to beneficial in cases of low antibody titers, which may be observed as false negatives at short incubation times. The high correlation of VIDEA to ELISA S/P rations indicates the ability of VIDEA as an assay for detecting anti-PRRS virus antibodies. The correlation with the ELISA S/P ratio of <0.4, which is the standard cut-off suggests that VIDEA may have equivalent sensitivity to ELISA.

Example 2

HIDEA

Devices of the invention with a coated surface and a permeable barrier are used wherein the barrier material is modified such that it defines one or more indentations in the surface of the barrier. Using agarose as a non-limiting example, one or more wells may be made in the agarose.

Each well was filled with 0.015 ml of test serum. Devices were incubated for about 12 to about 24 hours at room temperature (25° C.) to allow antibody diffusion and antigen-antibody reaction. Additional uses of the devices were conducted with 24 hour incubation times.

The gel was peeled off after an incubation and the dishes were washed 3 times with 5 to 8 ml of washing solution (PBS containing 0.05% Tween-20). Then 3 ml of commercially available peroxidase-conjugated rabbit anti-pig IgG (1 to 2 µg/ml) diluted in PBS was applied for 45 minutes at 25° C. After the dishes were washed again 3 times with washing solution, 5 ml of 1% agar in PBS containing substrate (5-aminosalicylic acid) and $H_2O_2$ at concentrations of 0.08% and 0.005%, respectively, was overlaid onto the dishes. The diameters of dark purple circular zones were measured in mm after 5 to 30 minutes of reaction for HIDEA. Tables 2 and 3 show different diameters of 14 sera tested under different conditions. The diameters of <7 mm are considered negative in HIDEA. Some of the ELISA negative sera showed positive results indicating better sensitivity for HIDEA. Results in Table 3 indicate a high repeatability of HIDEA.

TABLE 2

HIDEA diameters of swine sera with different ELISA S/P ratios using various incubation hours at room temperature (25 C.)

| Serum tested | Incubation hours | | | |
|---|---|---|---|---|
| | 15 h | 18 h | 20 h | 24 h |
| 1. PRRS-free | 3* | 6 | 4 | 5 |
| 2. PRRS-free | 4 | 6 | 4 | 5 |
| 3. ELISA S/P ratio** 0.06 | 7 | 8 | 9 | 9 |
| 4. ELISA S/P ratio 0.21 | 8 | 10 | 10 | 10 |
| 5. ELISA S/P ratio 0.73 | 8 | 11 | 11 | 11 |
| 6. ELISA S/P ratio 1.96 | 11 | 13 | 14 | 14 |
| 7. ELISA S/P ratio 2.83 | 12 | 14 | 15 | 15 |

*Diameter (mm) in HIDEA; greater than 7 mm are positive
**ELISA S/P ratio greater than 0.4 are positive

TABLE 3

Repeatability of HIDEA diameters for 7 sera with different ELISA S/P ratios and various incubation hours at room temperature (25 C.)

| Serum tested | 3 h | 6 h | 12 h | 15 h | 21 h | 24 h |
|---|---|---|---|---|---|---|
| 1. a. PRRS-free | 3* | 3 | 3 | 3 | 4 | 4 |
| b. PRRS-free | 3 | 3 | 3 | 3 | 4 | 4 |
| 2. a. PRRS-free | 3 | 3 | 3 | 3 | 4 | 4 |
| b. PRRS-free | 3 | 3 | 3 | 3 | 4 | 4 |
| 3. a. ELISA-neg | 3 | 3 | 3 | 3 | 4 | 4 |
| b. ELISA-neg | 3 | 3 | 3 | 3 | 4 | 4 |
| 4. a. ELISA-neg | 3 | 3 | 4 | 4 | 4 | 4 |
| b. ELISA-neg | 3 | 3 | 4 | 4 | 4 | 4 |

TABLE 3-continued

Repeatability of HIDEA diameters for 7 sera with different ELISA S/P ratios and various incubation hours at room temperature (25 C.)

| Serum tested | 3 h | 6 h | 12 h | 15 h | 21 h | 24 h |
|---|---|---|---|---|---|---|
| 5. a. ELISA S/P ratio 0.54 | 5 | 7 | 7 | 8 | 9 | 9 |
| b. ELISA S/P ratio 0.54 | 5 | 7 | 8 | 8 | 9 | 9 |
| 6. a. ELISA S/P ratio 1.80 | 5 | 7 | 7 | 7 | 10 | 10 |
| b. ELISA S/P ratio 1.80 | 5 | 7 | 7 | 8 | 10 | 10 |
| 7. a. ELISA S/P ratio 2.59 | 5 | 7 | 7 | 8 | 10 | 11 |
| b. ELISA S/P ratio 2.59 | 5 | 7 | 8 | 8 | 11 | 12 | a & b. each serum sample is tested twice by HIDEA for reproducibility
*Diameter (mm) in HIDEA; greater than 7 mm are positive
**ELISA S/P ratio greater than 0.4 are positive All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of preparing a vaccine composition containing PRRS virus proteins and antigens from PRRS virus infected cells, said method comprising
    a) providing a population of cells that have been infected with PRRS virus, wherein said cells produce viral proteins and antigens encoded by PRRS virus so that the majority of viral proteins and antigens encoded by the PRRS virus are either within the infected cells or associated with the cell membrane of the infected cells;
    b) isolating the PRRS virus infected cells, away from cell-free PRRS virus in the culture medium about the cells, to form isolated cells containing cell associated viral proteins and antigens encoded by PRRS virus;
    c) extracting or eluting the isolated cells with a detergent containing solution to form an extract or eluate containing the cell associated viral proteins and antigens along with cellular components; and
    d) combining said extract or eluate with an adjuvant to form a vaccine composition that protects a pig against PRRS virus infection.

2. The method of claim 1 wherein said detergent containing solution contains a non-ionic detergent.

3. The method of claim 1 wherein said extracting or eluting is for about 2 to about 15 hours at 4° C.

4. The method of claim 1 wherein said proteins and antigens include PRRS virus envelope proteins or the N protein.

5. The method of claim 1 wherein said proteins and antigens include a PRRS virus encoded glycoprotein.

6. The method of claim 1 wherein said proteins and antigens include a PRRS virus non-structural protein.

7. A method of preparing a vaccine composition containing PRRS virus proteins and antigens from PRRS virus infected cells, said method comprising
    a) providing a population of cells that have been infected with PRRS virus, wherein said cells produce viral proteins and antigens encoded by PRRS virus so that said cells produce cell-free PRRS virus into the culture medium;
    b) isolating the PRRS virus infected cells, away from cell-free PRRS virus in the culture medium about the cells, to form isolated cells containing cell associated viral proteins and antigens encoded by PRRS virus;
    c) extracting or eluting the isolated cells with a detergent containing solution to form an extract or eluate containing the cell associated viral proteins and antigens along with cellular components; and
    d) combining said extract or eluate with an adjuvant to form a vaccine composition that protects a pig against PRRS virus infection.

8. The method of claim 7 wherein said detergent containing solution contains a non-ionic detergent.

9. The method of claim 7 wherein said extracting or eluting is for about 2 to about 15 hours at 4° C.

10. The method of claim 7 wherein said proteins and antigens include PRRS virus envelope proteins or the N protein.

11. The method of claim 7 wherein said proteins and antigens include a PRRS virus encoded glycoprotein.

12. The method of claim 7 wherein said proteins and antigens include a PRRS virus non-structural protein.

* * * * *